United States Patent
Gauthier et al.

(10) Patent No.: US 11,382,602 B2
(45) Date of Patent: Jul. 12, 2022

(54) ULTRASOUND SYSTEMS FOR MULTI-PLANE ACQUISITION WITH SINGLE- OR BI-PLANE REAL-TIME IMAGING, AND METHODS OF OPERATION THEREOF

(71) Applicant: KONINKLIJKE PHILIPS N.V., Eindhoven (NL)

(72) Inventors: Thomas Patrice Jean Arsene Gauthier, Seattle, WA (US); Lars Jonas Olsson, Woodinville, WA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 413 days.

(21) Appl. No.: 16/534,734

(22) Filed: Aug. 7, 2019

(65) Prior Publication Data
US 2019/0357889 A1     Nov. 28, 2019

Related U.S. Application Data

(63) Continuation of application No. 15/113,474, filed as application No. PCT/IB2015/050384 on Jan. 19, 2015, now Pat. No. 10,405,835.
(Continued)

(51) Int. Cl.
*A61B 8/14* (2006.01)
*A61B 8/08* (2006.01)
(Continued)

(52) U.S. Cl.
CPC .............. *A61B 8/523* (2013.01); *A61B 8/085* (2013.01); *A61B 8/0891* (2013.01); *A61B 8/145* (2013.01);
(Continued)

(58) Field of Classification Search
CPC ....... A61B 8/085; A61B 8/0891; A61B 8/145; A61B 8/463; A61B 8/469; A61B 8/481;
(Continued)

(56) References Cited

U.S. PATENT DOCUMENTS

| | | |
|---|---|---|
| 5,531,224 A | 7/1996 | Ellis et al. |
| 6,056,691 A | 5/2000 | Urbano et al. |

(Continued)

FOREIGN PATENT DOCUMENTS

| | | | |
|---|---|---|---|
| EP | 1609421 A1 | 12/2005 | |
| JP | 5329155 A | 12/1993 | |

(Continued)

*Primary Examiner* — Mark D Remaly (57) ABSTRACT

The present invention relates to ultrasound imaging systems and methods, more particularly, to ultrasound imaging systems and methods for a multi-plane acquisition for single- or bi-plane real-time imaging modes suitable for ultrasound imaging applications, such as quantification of tumor blood flow and tumor fractional blood volume. An ultrasound imaging apparatus can determine a plurality of image planes to scan through a region of interest, acquire echo information corresponding to each of the image planes, generate image information for each of the image planes, store the image information corresponding to each of the image planes; and display an ultrasound image comprising the region of interest, wherein the ultrasound image is rendered from generated image information for a selected image plane of the plurality of image planes or a bi-plane that is at angle to the plurality of image planes.

15 Claims, 4 Drawing Sheets

Related U.S. Application Data (60) Provisional application No. 61/932,312, filed on Jan. 28, 2014.

(51) Int. Cl.
  *G01S 7/52* (2006.01)
  *A61B 8/00* (2006.01)

(52) U.S. Cl.
  CPC .............. *A61B 8/463* (2013.01); *A61B 8/469* (2013.01); *A61B 8/481* (2013.01); *A61B 8/5207* (2013.01); *A61B 8/5223* (2013.01); *A61B 8/54* (2013.01); *G01S 7/52074* (2013.01); *G01S 7/52084* (2013.01)

(58) Field of Classification Search
  CPC ..... A61B 8/5207; A61B 8/5223; A61B 8/523; A61B 8/54; G01S 7/52074; G01S 7/52084
  See application file for complete search history.

(56) References Cited

U.S. PATENT DOCUMENTS

| | | |
|---|---|---|
| 8,012,090 B2 | 9/2011 | Steen |
| 2003/0060710 A1* | 3/2003 | Salgo ................... G01S 7/52073 600/443 |
| 2003/0174872 A1 | 9/2003 | Chalana et al. |
| 2005/0283078 A1 | 12/2005 | Steen |
| 2008/0089571 A1 | 4/2008 | Kurita |
| 2012/0230575 A1 | 9/2012 | Gauthier et al. |
| 2012/0253190 A1 | 10/2012 | Gauthier et al. |
| 2014/0013849 A1 | 1/2014 | Gerard et al. |
| 2014/0236001 A1 | 8/2014 | Kondou |

FOREIGN PATENT DOCUMENTS

| | | |
|---|---|---|
| JP | 2011004949 A | 1/2011 |
| RU | 2532597 C1 | 11/2014 |
| WO | 2009044316 A1 | 4/2009 |
| WO | 2010032155 A1 | 3/2010 |
| WO | 2012080905 A1 | 6/2012 |

\* cited by examiner

ULTRASOUND SYSTEMS FOR MULTI-PLANE ACQUISITION WITH SINGLE- OR BI-PLANE REAL-TIME IMAGING, AND METHODS OF OPERATION THEREOF

CROSS-REFERENCE TO PRIOR APPLICATIONS

This application claims the benefit or priority of and describes relationships between the following applications: wherein this application is a continuation of U.S. patent application Ser. No. 15/113,474, filed Jul. 22, 2016, which is the National Stage of International Application No. PCT/IB2015/050384, filed Jan. 19, 2015, which claims the priority of U.S. application 61/932,312 filed Jan. 28, 2014, all of which are incorporated herein in whole by reference.

An accurate and early assessment of cancer treatment response is desirable for efficient cancer management and for the evaluation of new therapeutic compounds for cancer patients. Histological determination of a mean intra tumor micro vascular density (MVD) is the most commonly used method for assessing angiogenesis. However, MVD methods do not provide an accurate assessment of the functionality of tumor vessels because many poorly functioning or collapsed vessels have endothelial cells that are stained and counted and rely upon invasive techniques to obtain tissue samples for diagnosis. Therefore, determination of changes in MVD may not accurately reflect the effectiveness of an anti-angiogenic therapy. For many years, the standard way to assess tumor response to treatment has been to measure tumor size using axial computed tomography (CT) or magnetic resonance imaging (MM) imaging methods, and following a Response Evaluation Criteria in Solid Tumors (RECIST) guidelines and/or World Health Organization (WHO) guidelines. However, it may take several weeks to months for tumor morphology to noticeably change, hence diagnostic information based upon a change in tumor size may take from weeks to months to obtain. Thus, delay is undesirable and is frequently encountered when using image-based diagnostic methods to assess cancer treatments.

Newly introduced biological anti-cancer compounds, such as anti-angiogenic agents, can cause tumor enlargement before shrinkage, or may stabilize tumor growth to allow patients to live in symbiosis with their cancer. However, diagnosis based upon size criteria (e.g., change of tumor size over time) may not work in such cases. There is therefore clearly a need for a new imaging biomarker to assess tumor response. Such a new imaging biomarker may be used to assess early whether a particular therapeutic regimen is appropriate or effective following initiation of therapy, and it would have implications for both patient management and for drug development to support "go/no-go" decisions and accelerate, for example, clinical trials. Most cancer treatments currently available do not work immediately, do not cause complete necrosis, and/or may not dramatically affect tissue characteristics (compared with ablation therapy). It is therefore not straightforward to detect tumor change by current imaging methods unless the tumor size changes. Quantification of function of the tumor either by blood flow or by metabolism is therefore an attractive method to assess response to therapy such as such as anti-angiogenic therapy.

For example, a method known as contrast-enhanced ultrasound (CEUS) is one of three (together with Fludeoxyyglucose-positron emission tomography (FDG-PET) and dynamic contrast enhanced magnetic resonance imaging (DCE-MRI)) leading functional imaging methods which may be used to assess tumor response to anti-angiogenic therapy or the like. However, conventional CEUS methods can be inaccurate and difficult to perform. There is need for improved systems and methods that provide more accurate measurements and simpler image acquisition workflows.

The system(s), device(s), method(s), arrangements(s), user interface(s), computer program(s), processes, etc. (hereinafter each of which will be referred to as system, unless the context indicates otherwise), described herein address problems in prior art systems.

In accordance with embodiments of the present system, there is disclosed an ultrasound imaging system for imaging a region of interest of a subject. The system may include a controller that is configured to determine a number N of a plurality of image planes to scan through the region of interest, acquire echo information corresponding to each of the image planes in the plurality, generate image information for each of the image planes based upon the acquired echo information, store the image information corresponding to each of the image planes in a memory of the system; and render, in real time on a display, an ultrasound image comprising the region of interest, wherein the ultrasound image is rendered from generated image information for a single selected image plane of the plurality of image planes or a bi-plane that is orthogonal to the plurality of image planes.

Further, the controller may render, in real time on the display, lines or other characters or symbols that are overlaid on or positioned at the top and/or bottom of the ultrasound image rendered from the generated image information, the lines or other characters or symbols being indicative of the plurality of image planes scanned through the region of interest.

In addition, the controller may also render another ultrasound image on the display in real-time based on image information from one of the plurality of image planes and a selected line corresponding to the single selected image plane is displayed differently from remaining lines on the display, and wherein the selected line corresponds to an image plane that is at an angle (e.g., orthogonal) to the plurality of image planes.

It is also envisioned that the stored image information may include image information corresponding to the selected single image plane, which is rendered in real time, and image information corresponding to image planes, which are not displayed in real time, of the plurality of image planes. It is also envisioned that the controller may generate a time-intensity curve which represents contrast uptake based upon image information corresponding to the image planes which are not rendered in real time and the selected single image plane which is rendered in real time. Moreover, the controller may determine parameters including one or more of peak intensity, area under the curve, rise time, and mean transit time based upon the generated time intensity curve. It is also envisioned that a number of image planes rendered in real-time is independent of N. Moreover, N may be $2<N<N_{3D}$, where $N_{3D}$ is a typical number of planes acquired in real-time 3D imaging.

In accordance with embodiments of the present system, there is disclosed a method of displaying ultrasound images, and a computer program stored on a non-transitory computer readable memory medium, the computer program and the method being provided to perform the steps and features described for the ultrasound system.

The present invention is explained in further detail in the following exemplary embodiments and with reference to the In the drawings.

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well known devices, circuits, tools, techniques, and methods are omitted so as not to obscure the description of the present system. It should be expressly understood that the drawings are included for illustrative purposes and do not represent the entire scope of the present invention. In the accompanying drawings, like reference numbers in different drawings may designate similar elements.

In accordance with embodiments of the present system, there is disclosed an ultrasound system (e.g., a real-time two-dimensional (2D) and three-dimensional (3D) contrast-enhanced ultrasound (CEUS) system), which may perform off-line quantitative analysis of acquired image information. In some embodiments, ultrasound images from multiple scan planes or slices may be acquired in real-time, stored, and thereafter used for quantitative analysis. In one embodiment, quantification of tumor blood flow and tumor fractional blood volume may be performed off-line using, for example, cine loops of the acquired ultrasound images where data over the volume of the tumor can be collected and used for quantification. In this scenario, a user (e.g., an operator such as a sonographer, a doctor, etc.) may control an ultrasound imaging system to scan a plurality of image planes in an object-of-interest, such as a tumor, to acquire image information for each of the image planes to generate a plurality of ultrasound images of the object of interest. In certain embodiments, the collective image data for each of the plurality of image planes may form an image volume or 2D ultrasound images of the object-of-interest (e.g., the tumor) that can be used for various quantitative analyses. For example, image information from one or more of the image planes, which form the image volume, may be stored in a memory of the system for later use such as for post-processing. During post processing, the user may then position a region-of-interest (ROI) in the image volume for quantification and further analysis.

As will be described further herein, the plurality of images planes can be referred to as N image planes or N' image planes. N image planes are at an angle to N' image planes, e.g., at a 30°, 45°, 90°, or other desired angle. In some embodiments, the N (or N') image planes can be generated to be parallel to each other or at any angle relative (e.g., 90 degrees or orthogonal) to each other. In certain embodiments, a 2D array transducer can generate N image planes that fan out at a predetermined angle relative to each other. In some embodiments, the N image planes are orthogonal to at least one N' image plane. Sets of planes that are generated at an angle relative to each other may be spaced to capture data over about 90-110 degrees. In some embodiments, with a 2D matrix transducer the N image planes may correspond to azimuthal image planes and the N' image planes may correspond to elevational image planes or vice versa. The plurality of image planes may include N or N' image planes where N or N' is an integer greater than two. In some embodiments, a plurality of N image planes may be acquired and stored while only one N' image plane, i.e., a bi-plane image is displayed and/or stored during a scanning operation.

In accordance with some embodiments, each of the plurality of image planes (e.g., the image slices) may have a user-defined or default thickness (e.g., a slice thickness). The user may also control the location and/or orientation of one or more of the plurality of image planes. For example, the plurality of N (or N') image planes may be parallel to each other or at an angle to each other. The density or spacing between the image planes can also be defined. In some embodiments, an N' image plane orthogonal to the plurality of N image planes, can also be scanned and rendered for display. In certain embodiments, both sets of the plurality of N image planes and the plurality of N' image planes are used to generate ultrasound images. For example, a first set includes a plurality of N image planes, and a second set includes N' image planes that are orthogonal to the planes of the first set. In certain embodiments, a first set of a plurality of N image planes are fanned out in space and a second set of N' image planes are at an angle (e.g., orthogonal) to the N image planes.

In accordance with other embodiments, during the acquisition process, a single image plane of the plurality of image planes (e.g., the N image planes) will be displayed on the imaging system in real-time. In certain embodiments, a bi-plane (e.g., an orthogonal image plane) to the plurality of image planes (e.g., the N image planes) will be displayed on the imaging system in real-time. However, image information for each of the plurality of N image planes will be acquired and stored in a memory of the system for later use, such as for post processing off-line and/or for selection and display of one N image plane or an N' image plane at an angle (e.g., orthogonal) to the N image plane.

With regard to the post-processing, off-line post-processing for, e.g., a contrast-enhanced ultrasound application may be performed to determine parameters such as peak intensity area under a time-intensity curve, as well as other parameters such as rise time and mean transit time and other derived parameters which correlate with tumor blood flow and tumor fractional blood volume, and thus represent contrast uptake by the tumor. Using such a protocol, image information of each image plane (e.g., each image slice or scan plane) from the plurality of scanned image planes may be used to reduce or otherwise minimize errors due to slight changes of a location of an image plane and/or adjustments to the position of the region-of-interest. This may significantly reduce inaccuracy in the time-intensity curve and therefore derived parameters which are thought to correlate with tumor blood flow and tumor fractional blood volume due to changes of position of an image plane and/or adjustments to the region-of-interest.

Further, as tumors are never homogeneous, by providing quantitative information which may be derived from a plurality of scanned image planes of the tumor, embodiments of the present system may determine overall tumor vascularity with greater accuracy than may be derived from a single scanned image plane. Moreover, as embodiments of the present system may determine a balance between spatial and temporal contrast and determine a plurality of scan planes N based upon this balance, overall accuracy may surpass full 3D scans which may have limited temporal contrast.

Figure 1:
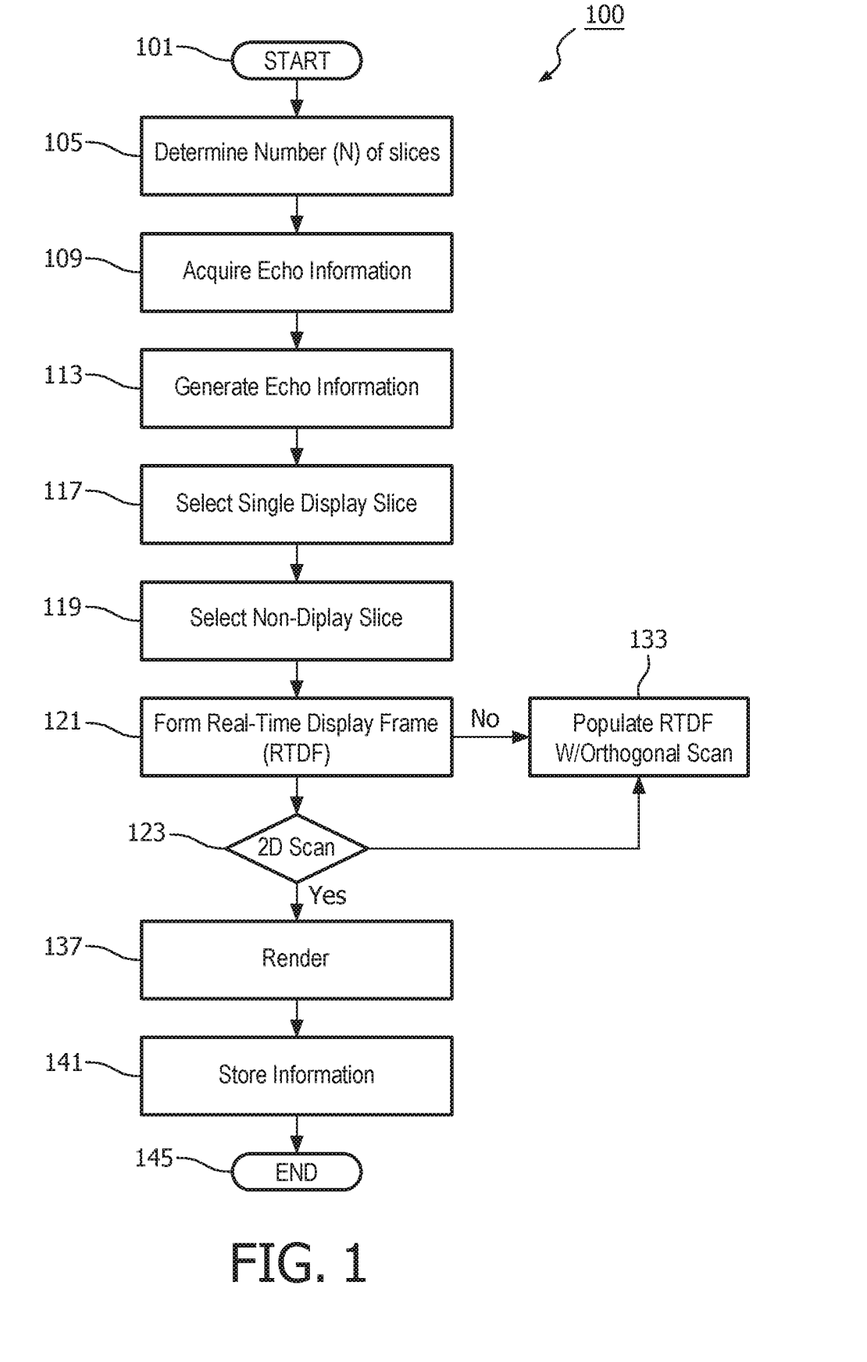
FIG. 1 shows a flow diagram that illustrates a process performed in accordance with embodiments of the present system.

FIG. 1 shows a flow diagram that illustrates a process 100 performed in accordance with embodiments of the present system. The process may perform a multi-slice acquisition in real time. The process 100 may be performed using one or more computers communicating over a network and may obtain information from, and/or store information to one or more memories which may be local and/or remote from each other. The process 100 can include one or more of the following acts performed by a processor or other device configured to perform the following acts. In some embodiments, the acts of process 100 may be performed using an ultrasound imaging system including the processor operating in accordance with embodiments of the present system. Further, one or more of these acts may be combined and/or separated into sub-acts, if desired, or one or more of these acts may be skipped depending upon settings. In operation, the process may start during act 101 and then proceed to act 105. It is noted that the process of FIG. 1 is one example embodiment of processes provided in the present disclosure. The process steps described further herein can be carried out, e.g., in a non-sequential fashion and in any desired order for producing a useful result in an imaging procedure. For example, the image planes that will be displayed can be changed while acquiring and displaying the image data. The number N of image planes being acquired can also be changed in real-time during imaging. Moreover, the image planes being stored can be changed and modified during imaging. For instance, a single set of planes or a loop of sets of image planes can be selected during an imaging procedure, or prior to using presets in the system.

Moving to act 105, the process can include determining a number of image planes to be scanned as the plurality of image planes. The discussion below will describe N image planes, but it can also apply to N' image planes. The value of the number of image planes used is represented by N, where N is an integer that can be greater than two. The value of N may be selected by the user of the system and defines a number of image planes (e.g., a plurality of fanned out image planes) to be acquired in a multi-slice image acquisition of an anatomical object of interest, such as a tumor. The N image planes may be at an angle to each other (e.g., fanned out) and may intersect the object-of-interest to be acquired. The N image planes that are at an angle to each other may be arranged in spacing that is representative of a sector image that is typically displayed in B-mode ultrasound imaging. The N planes may also be equidistant or not equidistant from each other.

In some embodiments, the number N of image planes used for a scanning procedure can abide by the following equation:

$$2 < N < N_{3D}, \quad \text{Eq. (1)}$$

where $N_{3D}$ is a typical number of planes acquired in real-time 3D imaging. Accordingly, the scan time using the present system is less than scan times used in typical 3D imaging. In some embodiments, a value of N may be set to about 5 to 10, and $N_{3d}$ could be between 32 to 160 frames. However, the number of N or N' image planes can be readily set by a user or provided, e.g., in a preset or default configuration for a given procedure. For example, in some embodiments, a number for N may be directly input from a user depending on the desired application. Accordingly, the process can include employing a user interface (UI) such as a menu or input keys which may be physical keys or software keys displayed on a touch sensitive display (e.g., a rotating knob, or other switches, such as a sliding switch, up-down arrows, menu list for selection etc.) with which a user may interact to enter or otherwise select a value of N. In some embodiments, physical keys and knobs associated with traditional ultrasound cart-based systems can be used.

In some embodiments, the value of N may be determined based upon, for example, a desired temporal or spatial resolution of an imaging volume. Thus, for example, as a user increases the temporal resolution, N may be decreased. In yet other embodiments, a default value for N may be obtained from a memory of the system. For example, N may have a default value of 8. Further, in yet other embodiments, the value of N may be set in accordance with user preferences obtained from a memory of the system. Accordingly, the process may identify a current user and obtain user settings corresponding with the identified user from a memory of the system. Thus, for a first user, the process may set the value of N=7 while for second user, the process may set the value of N=9. However, N may also be an even number.

In yet other embodiments, it is envisioned that the value of N may be determined in accordance with patient parameters such as a patient's age, height, weight, etc. In yet other embodiments, a value of N may be determined based upon differences in size of tissue being imaged for a given scan (e.g., a heart scan, a liver scan, a gallbladder scan, a pancreas scan, a kidney scan, a general intestinal scan, etc. and/or combinations thereof). For larger tissue structures, N may be greater.

Further, in yet other embodiments, the process may include determining whether previous scan information (e.g. from a previous scan of the current patient and which includes a value of N) is available. Accordingly, if it is determined that previous scan information is available, the system may use the same value for N as was used in the previous scan information (if N is available). This may provide for matching of the N scan planes in the current and previous scans for the same patient. However, if it is determined that that previous scan information is not available, the system may use a default value of N (e.g., 5). Further, if it is determined that N from the previous scan information is equal to 1 (e.g., only a single scan plane was obtained), the process may set N equal to a default value, e.g., 5.

In yet other embodiments, N may be determined based upon a look-up table. For example, parameters may be stored in a memory of the system in any suitable form such as a scan parameter table. Thereafter, the process may include using the scan parameter table to determine a value of N in accordance with entries of the scan parameter table. The scan parameter table may be set and/or reset by the system and/or user. Accordingly, the process may include providing the user with user interface with which the user may interact to set and/or reset the parameters of the scan parameter table, if desired.

As described herein, a single image plane of the plurality of image planes (e.g., the N image planes) can be rendered on a display of the imaging system in real-time, while a bi-plane (e.g., an orthogonal image plane of the plurality of image planes (e.g., the N image planes)) can also be rendered on the display in real-time. As will be referred to herein, a selected scan plane (SSP) (selected image plane) refers to a single selected image plane that is displayed among the plurality of image planes that are acquired. A selected scan plane (SSP) may also refer to two selected bi-plane (e.g., orthogonal) image planes that are displayed. For example, a selected N image plane and a respective N' image plane can be displayed in real-time. While the following description will mostly refer to acquiring and storing N image planes and displaying a single selected plane, it is equally applicable to embodiments where N, N' image planes are acquired and stored (e.g., where the N image planes are orthogonal to the N' image planes) and only two image planes of the acquired and stored N, N' image planes are actually displayed.

As will be described further below with reference to acts 117 and 119, the DNSP refers to scan planes which are not to be displayed and may be optionally included in some embodiments, if desired. For example, with regard to imaging a tissue of interest (e.g. a tumor or organ), six image planes (N=6) may intersect the tissue of interest during imaging. Scan plane 4 will be displayed during the scan. Scan planes that are not to be displayed (e.g., the DNSPs) are scan planes 1, 2, 3, 5, and 6. Any suitable format may be used. In some embodiments, the values of N, SSP, DNSPs, may be set in accordance with a user's settings. After completing act 105, the process may continue to act 109.

During act 109, the process may include acquiring echo information from the N image planes that intersect the object-of-interest (e.g., a tumor of the patient in the present example). Alternatively, N image planes that interest at an angle (e.g., orthogonally) with N' image planes are acquired during act 109. Accordingly, the process may include controlling an ultrasonic probe including a transducer array (e.g., a 2D matrix array transducer) to transmit ultrasonic pulses which intersect object of interest the N planes and to acquire echo information for each of the N planes in return. More particularly, the process may include controlling the probe(s) to obtain echo information corresponding with a real-time acquisition of the N scan planes.

During act 109, the process may further include obtaining echo information for at least one N' image plane (e.g., a bi-plane) that is at an angle (e.g., orthogonal) to the group of N image planes. If it is determined that only N image planes will be scanned, then the process will not obtain any N' image planes. If it is determined that a bi-plane image is to be acquired, the process may include obtaining the at least one N' image plane and, therefore, may include obtaining echo information for the at least one N' image plane. After completing act 109, the process may continue to act 113.

During act 113, the process may include generating image information for each of the N image planes based upon the acquired echo information received for each of the N image planes, respectively. The process may include generating the image information using any suitable methods generally well known in the art. In one embodiment, the process may include acquiring and generating multi-frame data using a Live-iSlice™ environment. The image information for each of the N scan planes may also be used to generate volume data. Further, the process may generate image information for the at least one N' image plane based upon the acquired echo information for the N' scan plane. After completing act 113, the process may continue to act 117.

During act 117, the process may include selecting images for real-time display during a scanning operation. In some embodiments, a single image plane of the N image planes is selected and displayed. In certain embodiments, a bi-plane image plane is displayed that is at an angle (e.g., orthogonal) to the N image planes, and if a plurality of N' image planes are acquired then one of the N' image planes is selected for display. The N image or bi-plane image (e.g., an N' image) selected for display can be displayed to a user in a suitable format, e.g., as a square, rectangle or as a sector image. The N image or bi-plane image (e.g., an N' image) may be selected by the process and/or user. For example, a default setting for which selected N or N' image may be obtained from a memory of the system and/or from a user through selection. Accordingly, the process may include providing a user with a user interface with which the user may interact (e.g., a knob, a menu, etc.) to select an image to display (e.g., before or during a scan, if desired).

In some embodiments, a process of elimination may be used to select the N image and/or N' image to display. For example, the displayed image may be selected among the N or N' image planes being acquired and stored. The other remaining N or N' image planes that are not displayed are referred to as DNSPs. In one embodiment, assuming that N=6, and the slices that are not to be displayed (e.g., DNSPs) are slices 1, 2, 3, 5, and 6, the process may determine that the image plane to display is the 4th slice. Thus, in some embodiments, the DNSPs are determined first and, thereafter, the image plane to display may be determined. In yet other embodiments the N image or N' image to display may be determined based upon a user's ID. Accordingly, in these embodiments, the process may identify the user, obtain the user's settings from a memory of the system, and thereafter set the N image planes or N' image planes in accordance with the user's settings. After completing act 117, the process may continue to act 119. It is also noted that acts 117 and 119 can be carried out in a different order of the process. For example, act 117 and/or 119 can be implemented after act 105 when the number of slices or image planes to be acquired is determined.

During act 119, the process may select the DNSPs. The DNSPs may include (N−1) of the N image planes, or (N'−1) of the N' image planes being acquired during a scan. The DNSPs are image planes that are stored but not displayed (e.g., non-display slices) in real time. The DNSPs may be selected using any suitable method such as from a memory of the system and/or from a user input. It is further envisioned that the DNSPs may further be set in accordance with the type of tissue being scanned (e.g., liver scan, heart scan, etc.). In yet other embodiments, once the value of N and the image plane to be displayed are determined the DNSPs may be determined using a process of elimination. Thus, if it is determined that N=7 and the image plane to be displayed is 4, then the process may determine that the DNSPs are 1, 2, 3, 5, 6, and 7. A similar process applies to selection among N' image planes that are orthogonal to the N image planes. In one embodiment, a single bi-plane image is selected, but other N' image planes can also be selected and displayed.

Referring back to the N image plane slices, in accordance with some embodiments, it is envisioned that the location, spacing, thickness, depth and/or orientation of the DNSPs slices may be set by the process and/or user. In some embodiments, if other values, settings, and/or parameters are necessary, the process may include obtaining corresponding default values from a memory of the system. After completing act 119, the process may continue to act 121.

During act 121, the process may include forming a real-time display frame (RTDF) for rendering on a display of the system. All ultrasound images generated of the object-of-interest which are to be displayed in real time, such as the SSP and, e.g., an orthogonal image plane to the SSP, are to populate the RTDF. However, images planes which are not to be displayed, such as the DNSPs, are not to populate the RTDF.

During act 123, the process may include determining whether only N image planes are to be acquired during imaging. This is referred to FIG. 1 as a 2D scan. If it is determined that only N image planes will be acquired, the process may continue to act 137. However, if it is determined that at least one N' image plane will be displayed and/or acquired, then the process may continue to act 133 in which the real-time display frame will display at least one of the N' image planes, such as an N' image plane orthogonal to the N image planes in the 2D scan. The system and/or user may select whether N and/or N' image planes will be stored and/or displayed. For example, in some embodiments, the process may provide a user with a user interface (e.g., knobs, menus) with which to interact with the system to select which image planes will be stored and/or displayed. This setting may be performed at any time such as a during an initial setup process. In yet other embodiments, depending upon a type of scan being performed (e.g., liver CEUS, etc.), the process may select a default configuration or user preferences for N and/or N' image planes to be stored and/or displayed.

Figure 2:
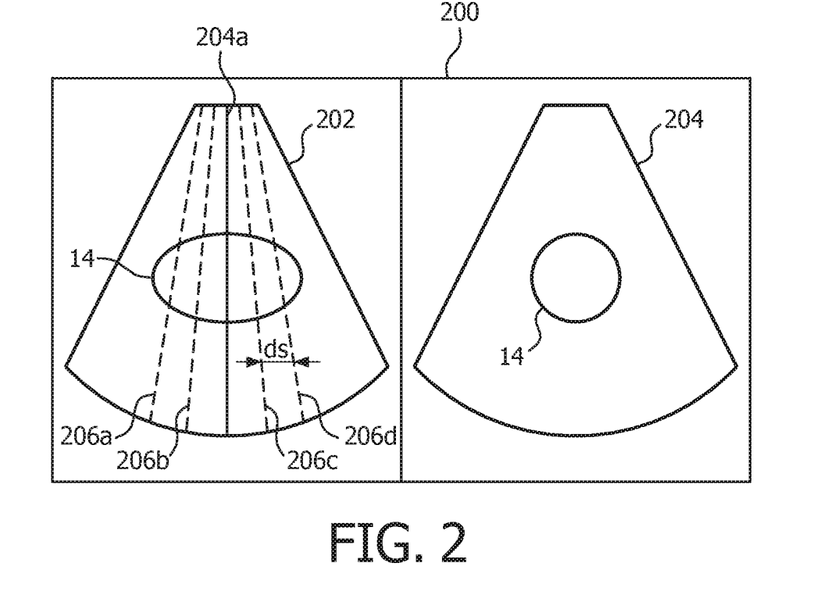
FIG. 2 shows a portion of a screenshot of a real-time display frame (RTDF) including a graph of image information for the selected single-plane (SSP) in accordance with embodiments of the present system.

The RTDF may include a continuous or discontinuous area(s) and may have a shape and/or size which may be selected by the system (e.g., default, by test type, by test parameters, etc.) or the user. Thus, the RTDF may be populated with image information for a selected N image plane (e.g., including a region-of-interest, if desired) and the image information for an N' image plane (e.g., an orthogonal N' image plane), and any associated information such as measurements, axes, slice locations, highlighting, etc. In some embodiments, the RTDF may include null information. For example, FIG. 2 shows a portion of a screenshot of the RTDF 200 including an ultrasound image 202 that corresponds to an N image plane (e.g., a slice within the region-of-interest, if desired), where image 202 includes image information of the region of interest, e.g., a tumor 14, in accordance with embodiments of the present system. The RTDF 200 may further include an ultrasound image 204 corresponding to an N' image plane that is at an angle (e.g., orthogonal) to the N image plane corresponding ultrasound image 202. A line 204a may be overlaid over the N image plane ultrasound image 202 to identify where the bi-plane ultrasound image 204 is located in relation. Other lines 206a, 206b, 206c, and 206d can be overlaid and displayed to show where other N' image planes are being imaged and stored, but not displayed. FIG. 2 shows solid and dashed lines over the image, but other indicators can be used to tell a user which lines are being displayed and which are just being stored. For example, opposing carats, stars, or other icons could be positioned on the outer edge of the image and shown, e.g., with different colors. The lines or other markings over the image could also be removed from the display to allow for better image viewing. In general, this information indicates to a user the number of the N of planes being acquired and their locations relative to each other. Of course, because the N image planes are orthogonal to the N' image planes, ultrasound image 202 could correspond to an N' image plane and ultrasound image 204 could correspond to an orthogonal N image plane. Similarly, the lines 204a and 206a-206d could correspond to N image planes. The ultrasound image 202 may be formed by the process using any suitable imaging method known in the art and could be displayed in a modified iSlice™ environment operating in accordance with embodiments of the present system. Also shown in FIG. 2, a distance ds indicates an angular distance between adjacent imaging planes of the N or N' imaging planes. In some embodiments, the image planes may be parallel in which ds may refer to units in mm. The angular distance ds between each of the imaging planes may be equal (e.g., N imaging planes may be equidistant from each other). However, in yet other embodiments, the imaging planes may be unequally spaced as may be set by the system and/or user. N and ds may be (inversely) related. For example, increasing N may cause ds to decrease and vice versa. After completing act 121, the process may continue to act 123.

Figure 3:
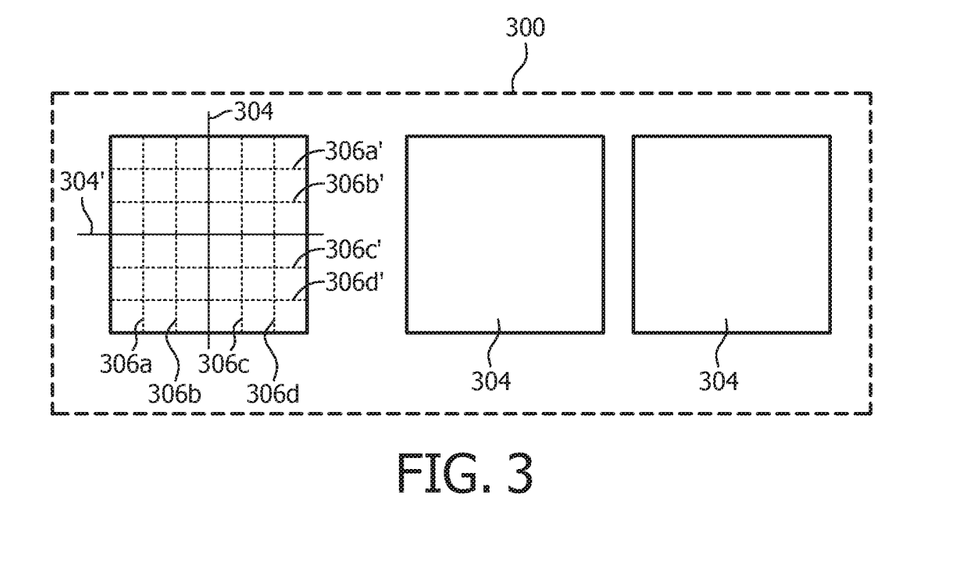
FIG. 3 shows a portion of a screenshot of the RTDF including the graph of the image information of the SSP and a graph including image information of an orthogonal scan plane in accordance with embodiments of the present system.

In some embodiments, act 133 can include populating the RTDF 200 with image information for both an ultrasound image 304 corresponding to an N image plane and an ultrasound image 304' corresponding to an N' image plane, as shown in FIG. 3. Further, the process may determine locations of each of the N image planes and show them as lines 306a-306d. Lines 306'a-306'd correspond to N' image planes that are orthogonal to the N image planes. The projection of the lines 304, 304', 306a-d, and 306'a-d can be shown in the RTDF 200 in a direction that is oriented orthogonal from the face of a 2D array transducer, such as an X-matrix transducer. This view can give the user an idea of how the image planes are oriented in respect to the azimuthal and elevational dimensions of the probe. In FIG. 3, the RTDF 300 includes the display of an N' image plane 304 and an orthogonal N' image plane 304'. As shown the images are displayed in rectangular form, but the sector shape image format shown in FIG. 2 can also be used. The solid lines 304 and 304' indicate the image plane that is being displayed, and the dotted lines (e.g., 306'a) indicate the DNSPs.

After completing act 133, the process may continue to act 137. In some embodiments, the process may fit the RTDF to information to be displayed therein, to a desired format, and/or to a rendering device such as a display of the system. During act 137, the process may render the ultrasound image 202 on a display of the system in real-time, or render at least one N' image plane (e.g., the two orthogonal ultrasound images 304, 304').

Figure 4:
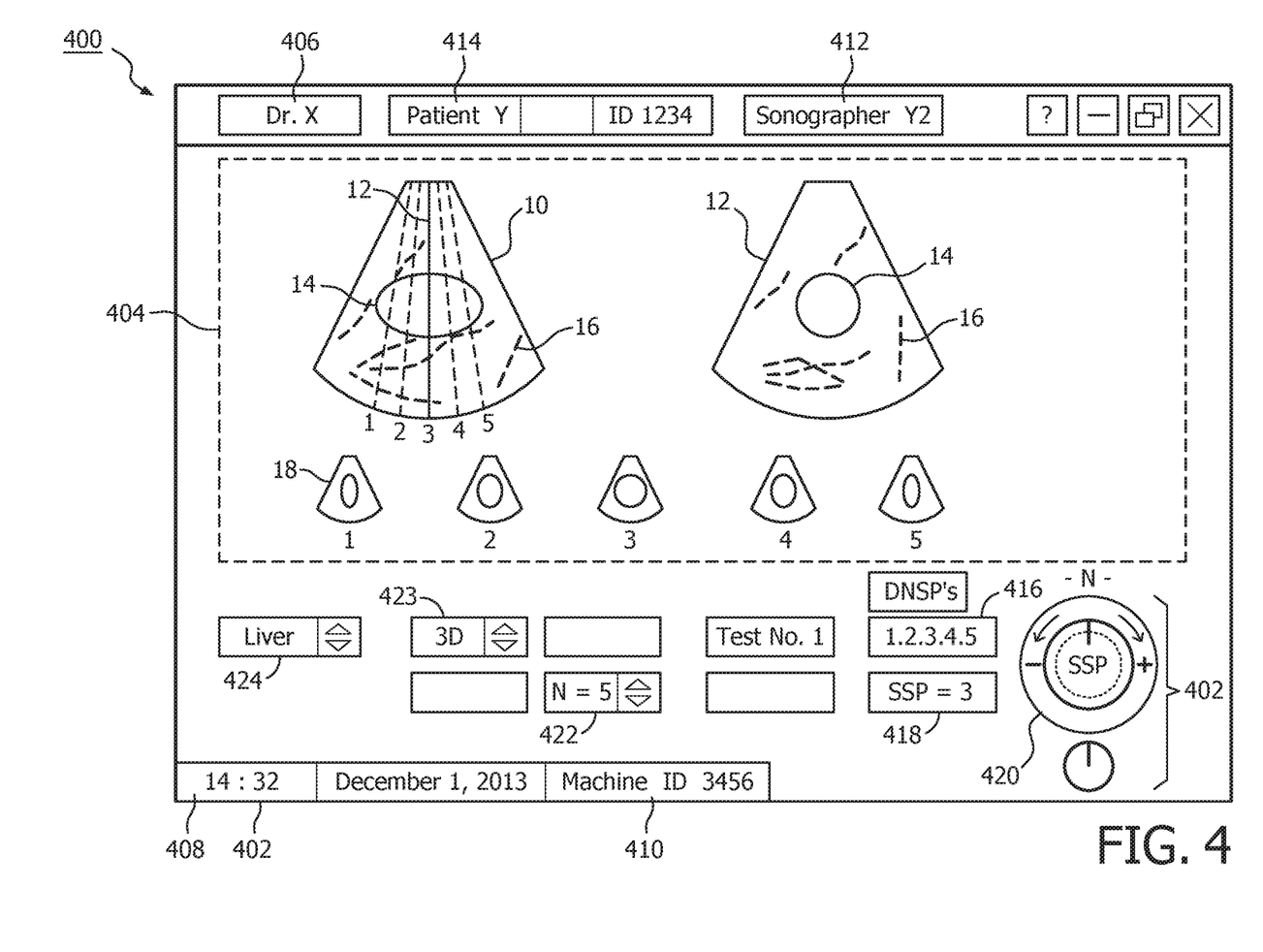
FIG. 4 shows a portion of a screen shot of a graphical user interface (GUI) including the RTDF in accordance with embodiments of the present system.

FIG. 4 shows a portion of a screen shot 400 of a graphical user interface (GUI) 402 including an RTDF 404. As shown in FIG. 4, the RTDF 404 includes two 2D images next to each other 10 and 12. Image 12 on the right side of FIG. 4 is an orthogonal image plane to the image plane acquired to display image 10. In this embodiment, the images 10 and 12 can be used to tell the user that they are aligned in the middle of the tumor 14. Dashed lines 16 in FIG. 4 are tissue structures. As shown, the lines overlaid on image 10 are numbered 1-5, where scan line 3 corresponds to the position of the image plane that is used to generate image 12. Lines 1, 2, 4, 5 correspond to other image planes that are orthogonal to the image plane used to generate image 10 (similar to 206a-206d in FIG. 2). Typically, lines 1, 2, 4 and 5 are stored by the system, but not shown for display. Only image 12, which corresponds to line 3, is displayed. In FIG. 4, the images corresponding to lines 1-5 are also shown as five smaller images 18 showing the different slices or cross sections of the tumor 14 in space. The cross section at the center of the tumor 14 is shown in images 12 and 3, where the center cross tumor section shown in image 3 is larger than the side or off-center cross sections shown in images of the tumor slices 1, 2 4, 5.

The solid line 3 in image 10 indicates the location of cross section within the tumor 14 (namely, though the center of the tumor 14) shown in an adjacent image that is being displayed in real-time as image 12 in the right panel of the interface. The dashed lines 1, 2, 4, 5 in image 10 indicate that these off-center tumor slices are available for selection by the user for display on the right panel of the interface (i.e., the side of FIG. 4) instead of the currently displayed image 12. Of course, if desired, more than one tumor slice may be displayed next to image 10, where even all the available tumor slices 1-5 may be simultaneously displayed. However, this clutters the GUI and may cause confusion. Accordingly, only the single ultrasound image corresponding to line 3 is displayed in image 12.

The dashed lines for 1, 2, 4, 5 also show the user what other images (besides the displayed image 12) are being acquired during the scan but not shown, as currently the selected image shown in the image 12 is the center tumor slice as this center slice is selected by the user as indicated by the solid line 3 in image 10. That is, the various cross-sections of the tumor 14 along image planes 1-5 are stored, while only image plane 3 (selected by the user) is being shown as the orthogonal image 12. The stored cross-section images can then be reviewed offline and used for quantification, for example, and/or also displayed in additional images next to currently images 10, 12 shown in FIG. 4.

It should be noted that while the user can also select the scan density or number of planes or slices of the object of interest, e.g., a tumor to be acquired in real time. Thus, instead of the 5 planes or slices shown in FIG. 4, the user may change the scan density, such as increase the real-time acquired slices from 5 to 10 for example. Further, additional slices may be acquired in real-time at different angles. For example, in addition to the 5 planes or slices 1-5, further 5 planes or slices 1'-5' (not shown) may also be acquired and displayed as an image, where the further slices 1'-5' are orthogonal to the slices 1-5. The two orthogonal middle slices 3, 3' may be used to better define the center of the tumor 14, as shown by a bulls-eye center. An additional image can displayed next to image 12, similar to image 304' shown displayed next to image 304 in FIG. 3, where the two images 304, 304' are orthogonal to each other for example.

The GUI 402 may include the RTDF 404 and a menu with which the user may interact with the process and/or system. Accordingly, the menu may include information such as values of N, and SSP, DNSPSs, a type of scan, Region of Interest, etc. which may be listed in boxes 422, 418, 416, 423, 424, respectively. Further, the UI 402 may include day, date, time information 408, information related to the scanner such as machine ID 410, information related to professionals who run and/or ordered the scan such as doctor ID 406 and user ID (e.g., sonographer) 412. The GUI 402 may further include information which may identify a patient such as patient ID 414. A soft key 420 may be selected to change a value the SSP, if desired. In yet further embodiments, a user may, for example, control the position and/or number of underlying acquired scan planes corresponding with the N and/or N' image slices using, for example, rotary knobs on the ultrasound scanner control panel, as may be desired. Alternatively, a touch panel may also be integrated into the system for user controls.

In some embodiments, selecting N image planes may automatically result in selection of N' image planes. For example, if N is selected to be 2 (i.e., SSP=2), then image information is displayed for both orthogonal slices 2 and 2' (i.e., SSP'=2), for display as two images, such as images 304, 304' shown in FIG. 3. After completing act 137, the process may continue to act 141.

During act 141, the process may include storing any or select information generated and/or otherwise used by the process in a memory of the system for later use. For example, the echo information, the generated image information for the each of N image planes, the image information for the orthogonal frame, the RTDF, parameter settings such as N, SSP, DNSPs, a patient's name, the professional performing the scan, the type of scan, the date of scan, a doctors name (who ordered the scan), etc., may be stored in a memory of the system for later use such as for off-line quantification or other post-processing. Additionally, the stored information may be used for determining parameters for later scans such as for later CEUS scans, etc. Data used by, obtained by, and/or otherwise generated by, the present system may be stored in any suitable archiving system such as a Picture Archiving System. Moreover, by controlling the value of N to be less than $N_{3D}$, the number of scan planes is reduced which can conserve system resources and reduce or prevent data workflow challenges. After completing act 141, the process may repeat act 105 or may continue to act 145, where it ends, if desired.

An off-line process operating in accordance with embodiments of the present system may also be used to perform quantitative analysis on the data generated by the process such as the image information for the N image planes. For example, quantification analysis could be used to sum up intensity in a region (e.g., a tumor) of an image during a CEUS procedure. The intensity quantification could be used to indicate an amount of vasculature present in the tumor, especially in applications where intensity is related to presence of contrast media in blood in the tissue. It is further envisioned that a modified Live-iSlice™ method operating in accordance with embodiments of the present system may be performed using a matrix transducer to provide enhanced frame rate and workflow over conventional methods.

Embodiments of the present system may perform data imaging in real-time for N image planes, where $2<N<N_{3D}$, where $N_{3D}$ is a typical number of planes acquired in real-time 3D imaging. Further, embodiments of the present system may allow the operator to control the number of scan planes N, so that the operator can adjust N to reach an acceptable trade-off between spatial sampling of the tumor and frame rate. However, during use, embodiments of the present system may render only a single scan plane of the N scan planes in real-time. Accordingly, as a user has to follow only a single scan plane in an enhanced user interface (UI) real time (as opposed to a plurality of scan planes in real-time), user distraction and confusion may be reduced or entirely prevented.

Embodiments of the present system may provide data at a higher volume rate than conventional real-time 3D systems. This may be advantageous when performing CEUS methods and may result in increased result accuracy. Further, by providing a user interface (UI) operating in accordance with embodiments of the present system, undue distraction at a critical time may be prevented. This may result in more accurate test results and/or fewer failed exams.

As analysis of a three-dimensional (3D) structure such as a tumor, based upon information obtained from using single scan plane may be unreliable, and as full 3D scans may have temporal and spatial limitations, embodiments of the present system provide advantages both of these methods. For example, by providing N scan planes wherein N is greater than 2 and less than a number (e.g., $N_{3D}$) of scan planes obtained using a full 3D scan, embodiments of the present system may enhance temporal and spatial contrast over existing systems thus allowing faster and more accurate scan analysis. This enhancement may be desirable for clinical validation and broad adoption of methods used by embodiments of the present system.

Moreover, by providing image information related to a plurality of scanned image planes (e.g., the N scan planes), it may be easier to match image information obtained from at least one currently-derived scan plane with image information of a scan plane from a previous scan (e.g., obtained earlier and stored in a memory of the system) for comparison using, for example image processing methods. Accordingly, by more closely matching current and previous scan planes, CEUS methods to determine parameters operating in accordance with embodiments of the present method may provide increased accuracy over conventional CEUS methods. This may be beneficial for therapy monitoring. Moreover, similar benefits may be obtained using embodiments of the present system for characterization studies using 2D CUES methods to collect information from a plurality of scan planes (such as N scan planes) of a tumor so as to characterize the tumor. For example, by obtaining information about a plurality of scan planes in the tumor, a characterization of the tumor which is more representative of characteristics of the overall tumor may be obtained as opposed to information collected using a single plane.

Figure 5:
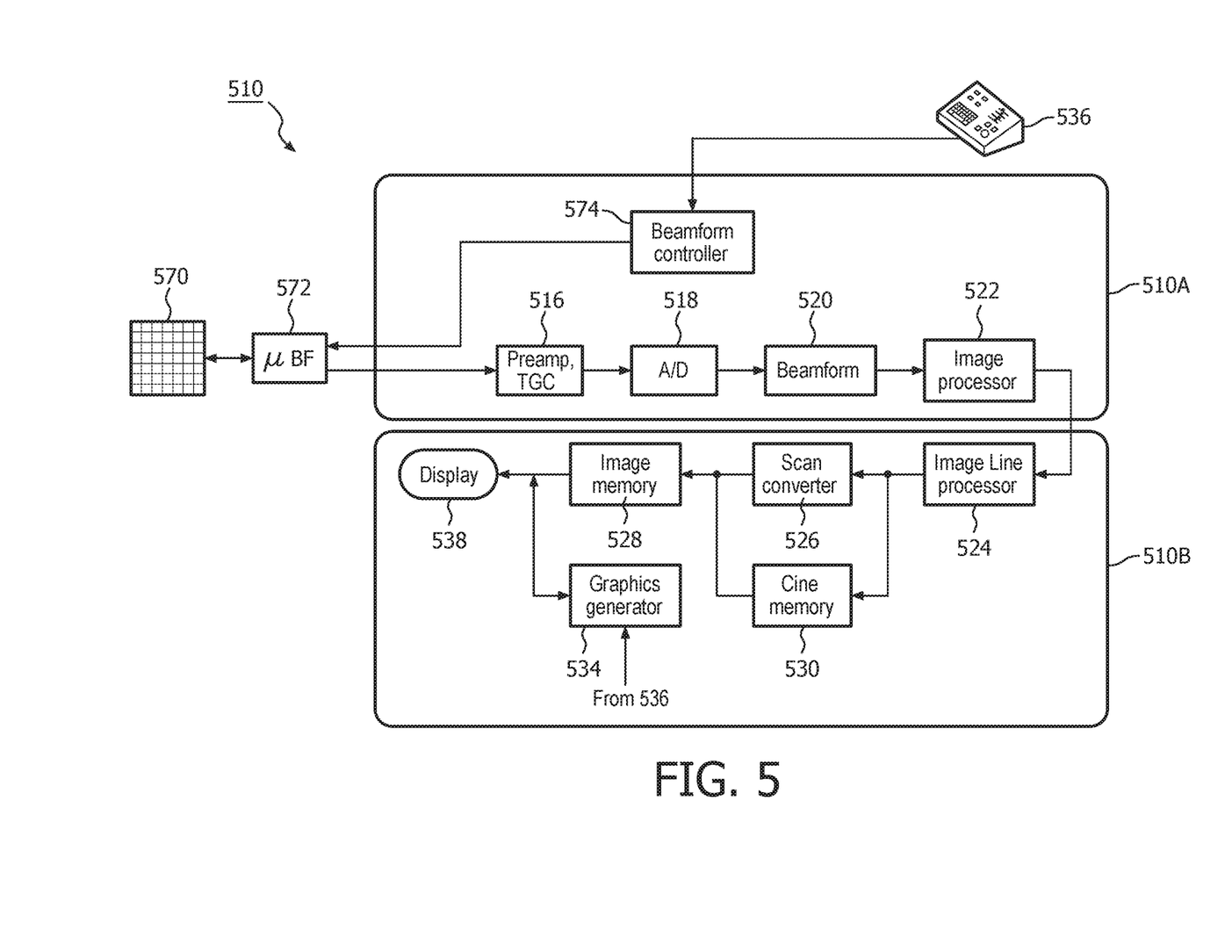
FIG. 5 illustrates in block diagram form an ultrasonic diagnostic imaging system constructed in accordance with the principles of the present invention.

Referring to FIG. 5, an ultrasound system 510 constructed in accordance with the principles of the present invention is shown in block diagram form. The ultrasound system is configured by two subsystems, a front end acquisition subsystem 510A and a display subsystem 510B. An ultrasound probe is coupled to the acquisition subsystem which includes a two-dimensional matrix array transducer 570 and a micro-beamformer 572. The micro-beamformer contains circuitry which control the signals applied to groups of elements ("patches") of the array transducer 570 and does some processing of the echo signals received by elements of each group. Micro-beamforming in the probe advantageously reduces the number of conductors in the cable between the probe and the ultrasound system and is described in U.S. Pat. No. 5,997,479 (Savord et al.) and in U.S. Pat. No. 6,436,048 (Pesque), and provides electronic steering of beams on transmit and receive for high frame rate real-time (live) imaging.

The probe is coupled to the acquisition subsystem 510A of the ultrasound system. The acquisition subsystem includes a beamform controller 574 which is responsive to a user control 536 and provides control signals to the microbeamformer 572, instructing the probe as to the timing, frequency, direction and focusing of transmit beams. The beamform controller also controls the beamforming of echo signals received by the acquisition subsystem by its control of analog-to-digital (A/D) converters 518 and a beamformer 520. Partially beamformed echo signals received by the probe are amplified by preamplifier and TGC (time gain control) circuitry 516 in the acquisition subsystem, then digitized by the A/D converters 518. The digitized echo signals are then formed into fully steered and focused beams by a main system beamformer 520. The echo signals are then processed by an image processor 522 which performs, e.g., digital filtering, B mode detection, and can also perform other signal processing such as harmonic separation, speckle reduction, and other desired image signal processing.

The echo signals produced by the acquisition subsystem 510A are coupled to the display subsystem 510B, which processes the echo signals for display in the desired image format. The echo signals are processed by an image line processor 524, which is capable of sampling the echo signals, splicing segments of beams into complete line signals, and averaging line signals for signal-to-noise improvement or flow persistence. The image lines for a 2D image are scan converted into the desired image format by a scan converter 526 which performs R-theta conversion as is known in the art. The scan converter can thus format rectilinear or sector image formats. The image is then stored in an image memory 528 from which it can be displayed on a display 538. The image in memory is also overlaid with graphics to be displayed with the image, which are generated by a graphics generator 534 which is responsive to the user control 536 so that the graphics produced are associated with the images of the display. Individual images or image sequences can be stored in a cine memory 530 during capture of image loops or sequences. With respect to FIG. 2, for example, the ultrasound imaging system is configured to display an ultrasound image 202 corresponding the selected N image plane and/or an ultrasound image 204 corresponding to an N' image plane as acquired by the matrix array transducer. The lines (e.g. 206a) can be displayed over the displayed image through the graphics generator.

The 2D array transducer can be operated to acquire image data from at least one N or N' image plane. For example, the 2D array transducer can be used to generate images that correspond to image planes 206a, 206b, 204a, 206c, and 206d of FIG. 2. When the matrix array probe is operated to scan both N image planes and N' image planes (e.g., as in FIG. 3), selected by the controls of the control panel 536, the beamform controller 574 is controlled to alternately acquire images of two different image planes in rapid, real-time succession. The controls of the control panel 536 can also be used to select the desired angle and orientation of the various imaging planes that are being scanned, e.g., the rotate, tilt, or elevation tilt can be modified. The live images of the two N and N' image planes can be displayed side-by-side as shown in FIG. 2. In one embodiment, the sonographer can hold the matrix array probe steady so that the target anatomy is constantly displayed in the N' plane image 202, and then manipulate a control of the control panel to tilt, rotate, or elevate the N' image plane to generate the image 204. In accordance with the principles of the present invention, the biplane images may be displayed, stored, and/or exported either in the standard format with both images in the same display frame, or as independent images. Moreover, while not shown, the system can further include a 3D processor, which can be used to display 3D volumes if desired.

Embodiments of the present system may be compatible with ultrasound systems having a matrix transducer such as Philips™ X5-1, X6-1, X7-2, and X7-2t matrix transducers and the like. It is further envisioned that embodiments of the present system may provide improved systems and methods for applications which may require (on-line or off-line) visualization and/or quantification of multiple scan planes such as tumor therapy monitoring.

While the present invention has been shown and described with reference to particular exemplary embodiments, it will be understood by those skilled in the art that present invention is not limited thereto, but that various changes in form and details, including the combination of various features and embodiments, may be made therein without departing from the spirit and scope of the invention.

Further variations of the present system would readily occur to a person of ordinary skill in the art and are encompassed by the following claims.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. The specification and drawings are to be regarded in an illustrative manner and are not intended to limit the scope of the appended claims.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function;
e) any of the disclosed elements may be comprised of hardware portions (e.g., including discrete and integrated electronic circuitry), software portions (e.g., computer programming), and any combination thereof;
f) hardware portions may be comprised of one or both of analog and digital portions;
g) any of the disclosed devices or portions thereof may be combined together or separated into further portions unless specifically stated otherwise;
h) no specific sequence of acts or steps is intended to be required unless specifically indicated; and
i) the term "plurality of" an element includes two or more of the claimed element, and does not imply any particular range of number of elements; that is, a plurality of elements may be as few as two elements, and may include an immeasurable number of elements.

What is claimed is:

1. An ultrasound imaging system comprising:
one or more processors configured to:
acquire echo information corresponding to a plurality of image planes in a region of interest, wherein the plurality of image planes comprises a first image plane and a second image plane at an angle to the first image plane;
generate, based on the echo information, a plurality of ultrasound images of the region of interest, wherein the plurality of ultrasound images comprises a first ultrasound image corresponding to the first image plane and a second ultrasound image corresponding to the second image plane;
output, to a graphical user interface on a display in communication with the one or more processors, the first ultrasound image;
receive, on the first ultrasound image, a selection corresponding to the second image plane; and
in response to receiving the selection, output the second ultrasound image to the graphical user interface such that the graphical user interface includes the first ultrasound image and the second ultrasound image to simultaneously display views of the region of interest at the angle relative to one another.

2. The ultrasound imaging system of claim 1, wherein the first ultrasound image and the second ultrasound image are proximate to one another in the graphical user interface.

3. The ultrasound imaging system of claim 1, wherein the first ultrasound image and the second ultrasound image are two-dimensional ultrasound images.

4. The ultrasound imaging system of claim 1, wherein the angle comprises 90 degrees such that the first image plane and the second image plane are orthogonal.

5. The ultrasound imaging system of claim 1, wherein the one or more processors are configured to define a selectable region of the first ultrasound image corresponding to the second image plane, wherein the one or more processors receiving the selection corresponding to the second image plane comprises the one or more processors receiving the selection of the selectable region.

6. The ultrasound imaging system of claim 1, wherein the one or more processors are configured to define a plurality of selectable regions corresponding to the plurality of image planes, wherein the selectable region corresponding to the second image plane is one of the plurality of selectable regions.

7. The ultrasound imaging system of claim 1, further comprising the display, wherein the display is a touch sensitive display, and wherein the one or more processors receiving the selection comprises the one or more processors receiving a user input via the touch sensitive display.

8. The ultrasound imaging system of claim 1, further comprising a memory in communication with the one or more processors, wherein the one or more processors are configured store the plurality of ultrasound images in the memory, wherein the plurality of ultrasound images comprises the first ultrasound image, the second ultrasound image, and at one ultrasound image that is not displayed.

9. The ultrasound imaging system of claim 8, wherein the one or more processors is configured to select, from among the plurality of ultrasound images, the first ultrasound image and the second ultrasound image for display.

10. The ultrasound imaging system of claim 9, wherein the one or more processors selecting the first ultrasound image and the second ultrasound image for display comprises the one or more processors receiving a selection of at least one of the plurality of ultrasound images that are not for display.

11. The ultrasound imaging system of claim 8, wherein the one or more processors are configured to output, to the graphical user interface, at least a third ultrasound image of the plurality of ultrasound images such that the graphical user interface includes first ultrasound image, the second ultrasound image, and the third ultrasound image.

12. The ultrasound imaging system of claim 11, wherein the first ultrasound image and the second ultrasound image are displayed larger than the third ultrasound image in the graphical user interface.

13. The ultrasound imaging system of claim 1, further comprising a memory in communication with the one or more processors, wherein the one or more processors are configured to:
generate image information based on the echo information;
store the image information in the memory; and generate a time-intensity curve which represents contrast uptake, through quantitative post-processing of the image information.

14. The ultrasound imaging system of claim 13, wherein the one or more processors are further configured to determine parameters comprising at least one of peak intensity, area under the time-intensity curve, rise time, or mean transit time through quantitative analysis of the time-intensity curve.

15. The ultrasound imaging system of claim 1,
- wherein the plurality of image planes further comprises a third image plane at a further angle to the first image plane,
- wherein the plurality of ultrasound images further comprises a third ultrasound image corresponding to the third image plane,
- wherein the selection, on the first ultrasound image, corresponding to the second image plane comprises a choice of the second image plane as between the second image plane and the third image plane.

* * * * *